United States Patent [19]

Biche et al.

[11] 4,220,387
[45] Sep. 2, 1980

[54] MEDICAL CLIP

[75] Inventors: Barton A. Biche, Newbury Park; Lawrence J. Stupay, Thousand Oaks, both of Calif.

[73] Assignee: Bunker Ramo Corporation, Oak Brook, Ill.

[21] Appl. No.: 25,699

[22] Filed: Apr. 2, 1979

[51] Int. Cl.³ ............................................. H01R 11/22
[52] U.S. Cl. ............................. 339/61 R; 339/113 R; 339/261
[58] Field of Search ................. 339/61 R, 101, 113 R, 339/113 B, 113 L, 147 P, 200 P, 255 P, 260, 261; 128/639-641

[56] References Cited

U.S. PATENT DOCUMENTS

| | | | |
|---|---|---|---|
| 909,481 | 1/1909 | Tregoning | 339/261 |
| 1,195,079 | 8/1916 | Peterson | 339/261 |
| 1,294,656 | 2/1919 | Hammond | 339/261 |
| 1,651,294 | 11/1927 | Rumore | 339/255 P |
| 2,035,345 | 3/1936 | Schaefer | 339/101 |
| 3,445,805 | 5/1969 | McLoad | 339/113 R |
| 3,606,881 | 9/1971 | Woodson | 128/641 |
| 3,611,247 | 10/1971 | Adams et al. | 339/196 R |
| 3,651,447 | 3/1972 | Branco et al. | 339/260 |
| 3,662,322 | 5/1972 | Morrison | 339/113 R |
| 3,740,703 | 6/1973 | Sessions | 339/261 |
| 3,774,143 | 11/1973 | Lopin | 339/61 R |
| 3,829,826 | 8/1974 | Brown et al. | 339/260 |
| 4,029,381 | 6/1977 | Tarrall et al. | 339/61 R |
| 4,040,697 | 8/1977 | Ramsay et al. | 339/61 R |
| 4,072,388 | 2/1978 | Dunn | 339/261 |

FOREIGN PATENT DOCUMENTS

| | | | |
|---|---|---|---|
| 1490489 | 8/1969 | Fed. Rep. of Germany | 339/261 |
| 2248786 | 4/1974 | Fed. Rep. of Germany | 339/113 R |
| 292340 | 6/1928 | United Kingdom | 339/261 |

*Primary Examiner*—Neil Abrams
*Attorney, Agent, or Firm*—F. M. Arbuckle; J. R. Hoffman

[57] ABSTRACT

A medical terminal clip is disclosed, particularly for use in connecting a lead wire or conductor to an electrode conventionally secured to the skin surface of a human or animal. The electrode comprises a male projection of the buttontype with an enlarged diameter head portion disposed within a recessed area of the electrode. The clip is generally V or wishbone shaped and includes a pair of support arms secured together at one end and normally spaced from each other at the other end. The arms carry resilient conductive loops normally biased out of overlapping condition but movable upon the application of external force into an overlapped condition wherein the clip may be applied over the head portion of the electrode. The support arms have offset depending shoulder portions from which the conductive loops extend and which are positionable within the recessed area of the electrode when the arms are moved toward each other. The support arms are integrally formed of resilient dielectric plastic material in an initial unstressed generally V-shape, with a female socket embedded in the plastic and electrically connected by conductor means to the conductive loops. Replaceable or interchangeable identification means is removably mounted on the clip in the area of the female socket, and a strain relief cover is removably positionable on the clip over said female socket and over said identification means to provide strain relief for the connection to a lead wire, and the cover is at least in part transparent to provide visual observation of the identification means.

10 Claims, 8 Drawing Figures

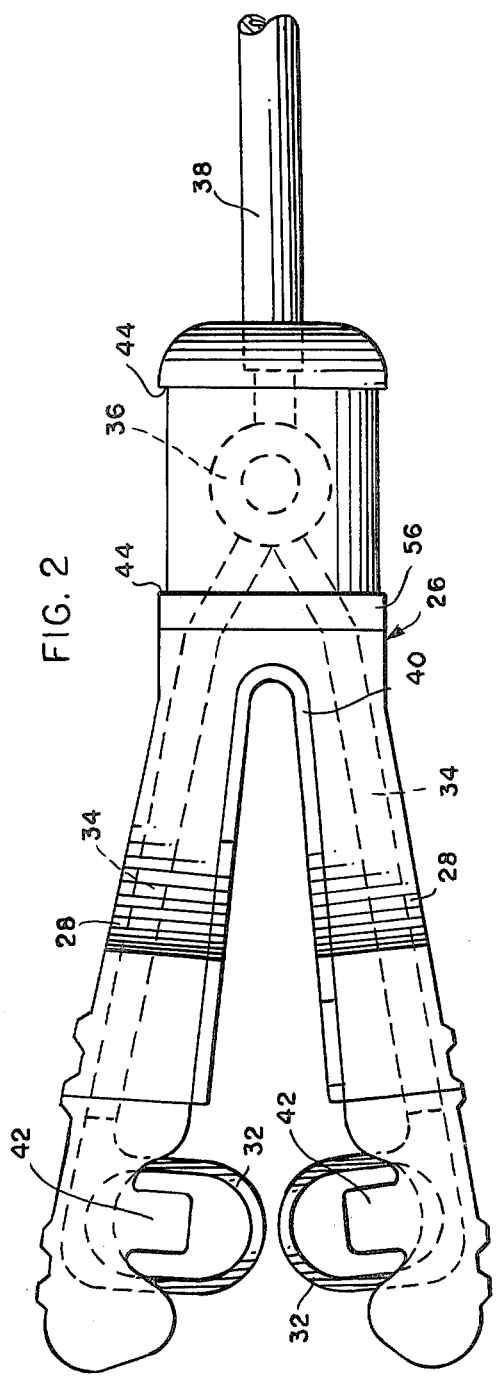
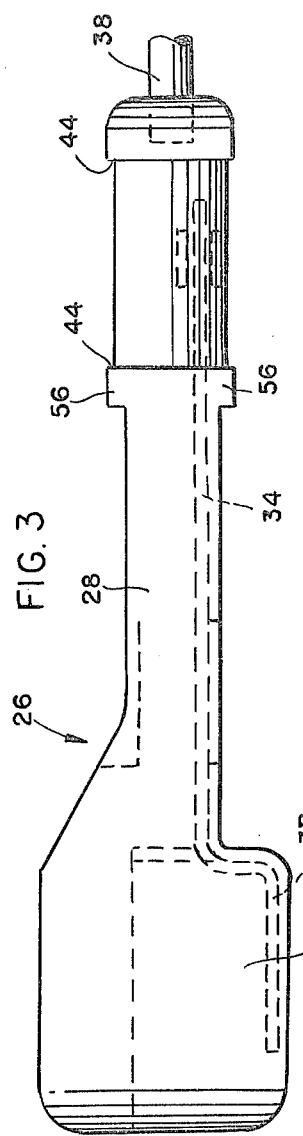
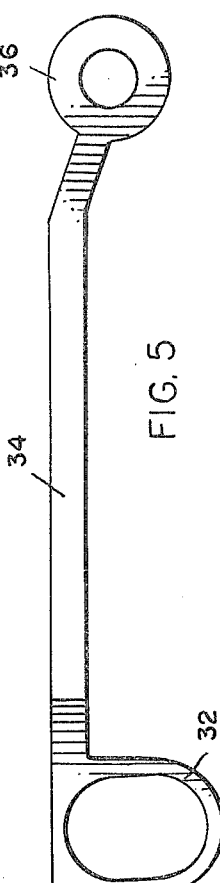
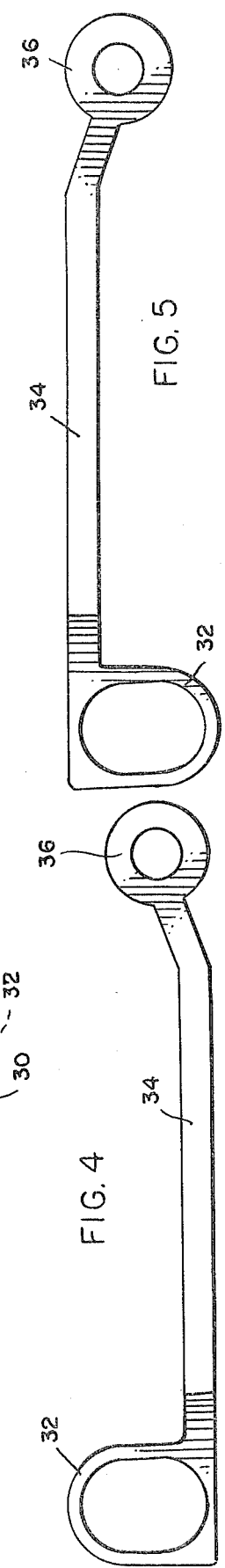
FIG. 2
FIG. 3
FIG. 4
FIG. 5

MEDICAL CLIP

BACKGROUND OF THE INVENTION

This invention relates to a terminal clip for electrically connecting an electrical conductor cable associated with medical equipment or the like to conventional male electrodes.

Such electrodes as described above are well known in the medical field and typically comprise a conductive male projection having an enlarged head for association with the terminal clip and a base carried by a patch, or the like, adhesively secured to or associated with the common anatomical positions such as left arm, right arm, left leg, right leg, and particular torso areas of a human or animal. The electrodes are then connected, by terminal clips, to a cable or lead wire to a medical machine or instrument, such as electrocardiographic machine.

One of the problems with electrodes of the character described, with a male projection protruding from a larger, generally flat base carried by a patch or the like, is that the male projection provides a convenient finger grip for the electrode which, during manipulation, may become damaged. The male projection, simply due to it being a protruding portion of the electrode, is susceptible to damage other than when used as a finger grip. Consequently, many electrodes are being manufactured wherein the male projection is disposed within a recessed area of the electrode for protection purposes. In some instances, this recess area is formed by providing a circular ring on the top of the flat base of the electrode, spaced from and surrounding the male projection. Many terminal clips presently available cannot be used with an electrode having the male projection seated within a recessed area of the electrode.

This invention is directed to providing a new and improved terminal clip of the character described for solving the aforesaid problems in an integrally molded construction having new and improved interchangeable identification means and a new and improved strain relief means.

SUMMARY OF THE INVENTION

A principle object of the present invention is to provide a new and improved terminal clip for electrically connecting an electrical conductor cable associated with medical equipment or the like to electrodes secured or associated with various anatomical positions of a patient.

Another object of the invention is to provide a new and improved terminal clip of the character described which is specially adapted for use with an electrode wherein the male projection portion thereof is disposed within a recessed area of the electrode.

A further object of the present invention is to provide a terminal clip of the character described which has a novel interchangeable identification means on the terminal body member of the clip, along with a strain relief cover positionable over the body member and the identification means, the strain relief cover member being transparent to provide visual observation of the covered identification means.

Still another object of the present invention is to provide a terminal clip of the character described wherein the lead wire or cable to the medical equipment is connected to the terminal clip by a releasable male-female connection means, and wherein the strain relief cover member not only covers the identification means, but also covers and protects the cable connection means.

In the examplary embodiment of the invention, a terminal clip is provided for use with electrodes of the general type having a male projection with an enlarged diameter head portion thereon, the male projection being disposed within a recessed area of the electrode. A pair of support arms formed integrally of resilient dielectric plastic material are secured together at one end and normally spaced from each other at the other end in an initial unstressed, generally V-shape. The support arms have offset depending shoulder portions spaced from the common integral end thereof, the shoulder portions being positionable within the recessed area of the electrode when the arms are moved toward each other. A conductive loop extends from the depending shoulder portion of each of the support arms toward the other arm, whereby the conductive loops are overlappable with each other when the arms are moved toward each other to form an aligned aperture sufficiently large to pass over the head portion of the electrode when the loops are so overlapped.

In the form of the invention shown herein, a female connector or socket is embedded in the common connecting end of the integrally formed support arms, and electrical conductor means is embedded within the arms connecting the conductive loops to the female connector. In the examplary embodiment of the invention, the conductive loops are substantially flat, thin members to provide for enhanced gripping of the head portion of the electrode. The conductive loops are defined by an offset end of a generally L-shaped conductive member, with the leg of the L-shape being embedded within the support arms and connected at its rearward end to the female connector.

Another feature of the invention is the provision of a V-shaped spring disposed between the integrally formed support arms generally at the apex of the V-shape thereof, to provide additional resiliency to accomodate for any resilient memory of the dielectric plastic material.

The terminal clip of the present invention further includes identification means for identifying anatomical positions or the like of a patient. The identification means comprises a thin plastic open-ended band positionable within a peripheral recess of the terminal clip, generally at the rear end thereof. The band is removable for replacing or interchanging the identification means to permit common clips to identify different anatomical positions by a single terminal clip. A strain relief cover member is removably positionable over the identification means not only to provide strain relief for the female connector for the lead wire or cable, but the strain relief cover provides protection for the interchangeable identification means and at least in part is transparent to provide visual observation of the identification means through the cover.

Other objects, features and advantages of the invention will be apparent from the following detailed description taken in connection with accompanying drawings.

DESCRIPTION OF THE DRAWINGS

FIG. 2 is a top plan view of the terminal clip, with the identification band and strain relief cover removed;

FIG. 3 is a side elevational view of the terminal clip shown in FIG. 2;

FIG. 4 is a top plan view of the unitary conductive loop and interior electrical conductor means for the bottom support arm as shown in FIG. 2;

FIG. 5 is a top plan view of the unitary conductive loop and interior electrical conductor means for the top support arm as shown in FIG. 2;

DETAILED DESCRIPTION OF THE INVENTION

Figure 1:
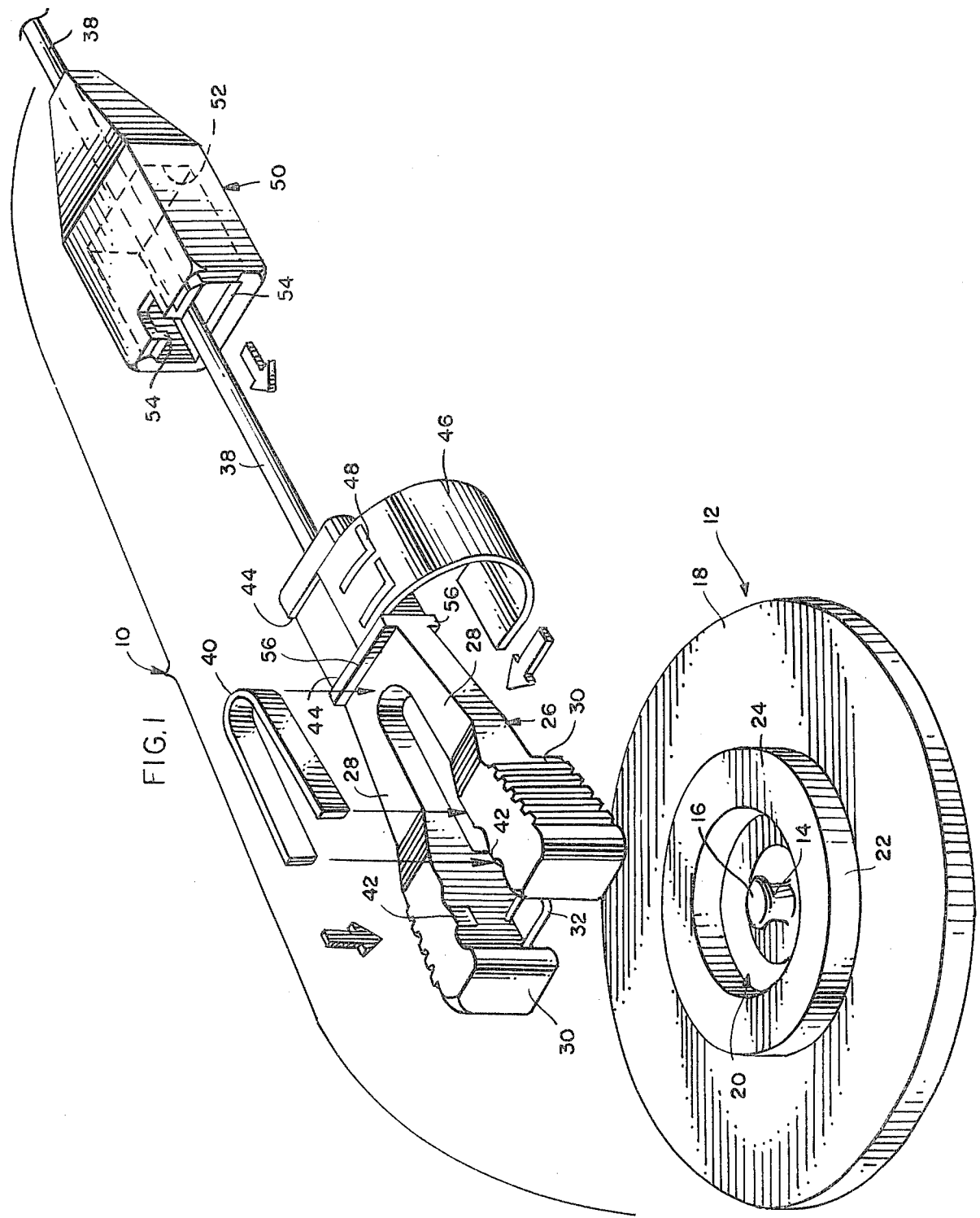
FIG. 1 is an exploded front perspective view of the terminal clip of the present invention and the various components thereof, in association with a conventional electrode having a recessed male projection.

Referring to the drawings in greater detail, and first to FIG. 1, a terminal clip, generally designated 10, is provided for use with electrodes, generally designated 12, of the general type having a male projection 14 with an enlarged diameter head portion 16. The male projection 14 protrudes upwardly from a flat disc-like base 18 which, in many instances, is adhesively secured to various anatomical positions of a patient. The male projection 14 is disposed within a recessed area, generally designated 20, formed by an upwardly protruding circular ring 22 surrounding and spaced from the male projection 14. The ring 22 has an upper flat surface 24 which generally is slightly higher than the male projection to provide protection therefor. In addition, the ring 24, due to the overall relatively small size of the electrode 12, prevents the usage of the male projection 14 as a finger grip for the electrode.

Figure 8:
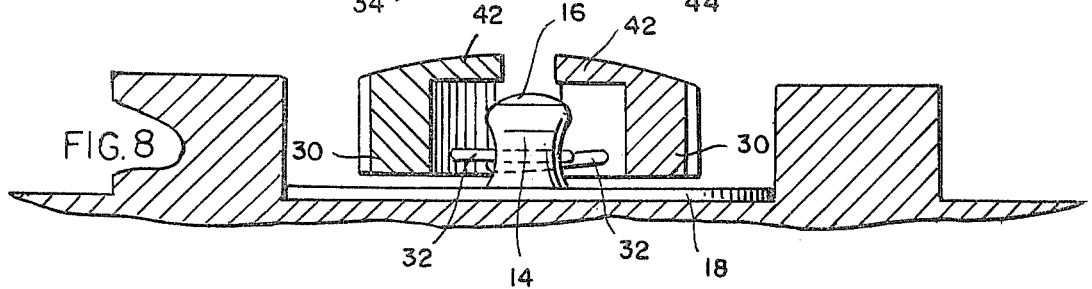
FIG. 8 is a fragmented, vertical sectional view through the support arms of the terminal clip, with the conductive loops positioned about the male projectin of an electrode of the character described.

The terminal clip 10 includes a terminal body member, generally designated 26, integrally molded of resilient dielectric plastic material in an initial unstressed generally V-shape. The body member includes a pair of support arms 28 secured together at their rearward ends and normally spaced from each other at the opposite or forward ends. As best seen in FIGS. 1 and 3, the support arms 28 include offset, depending shoulder portions 30 on the underside thereof, generally at the distal ends of the arms. These shoulder portions 30 are positionable within the recessed area 20 of the electrode 12 when the arms are moved toward each other, as seen in FIG. 8.

A conductive loop 32 (see FIGS 2-5) extends inwardly from the depending shoulder portion 30 of each of the support arms 28, toward the other support arms. As seen in FIG. 8, the conductive loops 32 are overlappable with each other when the arms are moved toward each other to form an aligned aperture sufficiently large to pass over the head portion 16 of the male projection 14 when so overlapped.

The conductive loops 32 are designed by an offset end of a generally L-shaped conductive member which is shown best in FIG. 3. Each member comprises the conductive loop 32 at one end thereof, an intermediate leg portion 34 extending rearwardly from the loop and offset upwardly therefrom (see FIG. 3) and a rear ring portion 36 which is utilized for connection to a lead wire or cable 38 which leads to a medical machine or instrument such as an electrocardiographic machine. As best seen in FIGS. 2 and 3, the L-shaped conductive members, comprising the loop 32, leg 34 and ring 36, are embedded within the arms 28 and rear end of the terminal clip body member 26, with the conductive loops 32 exposed exteriorly of the molded plastic support arms 28. As best seen in FIG. 3, the L-shaped conductive members, particularly the conductive loops 32, are substantially flat thin members to provide for enhanced gripping of the male projection 14 beneath the enlarged head portion 16 thereof.

Referring to FIGS. 1 and 2, a generally V-shaped metal spring 40 is disposed between the support arms 28 at the inner apex of the V-shape thereof. This spring is electrically isolated from the conductor legs 34 by the dielectric plastic material of the support arms 28. This V-shape spring 40 provides additional resiliency for the terminal clip to accomodate for any resilient memory of the dielectric plastic material of the clip.

It should be pointed out that the conductive loops 32 are sufficiently resilient, due to the thin flat nature thereof, so as to deflect under the head portion 16 of the male projection 14 to pivotally move about an axis generally parallel to the support arms 28 and spaced from the center of the head portion 16 to accomodate movement of the clip away from the electrode without disassembly therefrom.

Referring to FIGS. 2 and 8, a shelf 42 is formed integrally with each support arm 28 generally at the top thereof, with the shelf protruding inwardly toward the other arm over at least a portion of the area encompassed by the respective conductive loop 32. These shelves 42 provide cover means for the male projection 14 and prevents inadvertant touching of the electrode by a patient or by a medical attendant.

Referring to FIGS. 1 through 3, identification means is provided on the terminal body member 26, such as for identifying different anatomical positions or the like. More particularly, a peripheral recessed area at the rear end of the body member 26 is defined by a pair of opposed spaced shoulders 44. A flexible plastic band 46 is bent into a shape so as to be positionable between the shoulders 44, as is shown initially in FIG. 1. The band has identifying means 48 thereon for identifying the anatomical postions of the patient, such as the "LL" identification shown in FIG. 1 representing the left leg of the patient. This identifying band 46 is readily removable from the recessed area between the shoulders 44 of the terminal body member 26 for replacing or interchanging the identification means to permit different anatomical positions to be identified by a single terminal clip, or a terminal clip in a set thereof.

Referring again to FIG. 1, a strain relief cover, generally designated 50, is positionable over the rearward end of the terminal body member 26 and over the identification band 46 for plural purposes: namely, to provide strain relief for the connection at the rear of the terminal body member with the lead wire or cable 38, and to cover and hold the identification band 46 in position between the shoulders 44. The strain relief cover member 50 is transparent to provide visual observation of the identifying means or symbols 48 through the cover. The cover has an interior cavity 52 which surrounds the identification band 46 and within which the rear end of the terminal body member 26 is disposed. The front of the cavity 52 has a peripheral inwardly directed flange 54 which snap-fits in front of upper and lower flanges 56 on the terminal body member 26. The flanges 56 form the front shoulders 44 defining the recessed area for receiving the identification band 46. Thus, the strain relief cover member 50 is readily removable out of its snap-fit relation on the rear end of the terminal body member 26 for replacing or interchanging the identification band 46, as well as providing acsess to the connection between the interior conductor of the clip and the lead wire or cable 38 leading to the medical equipment.

Figure 7:
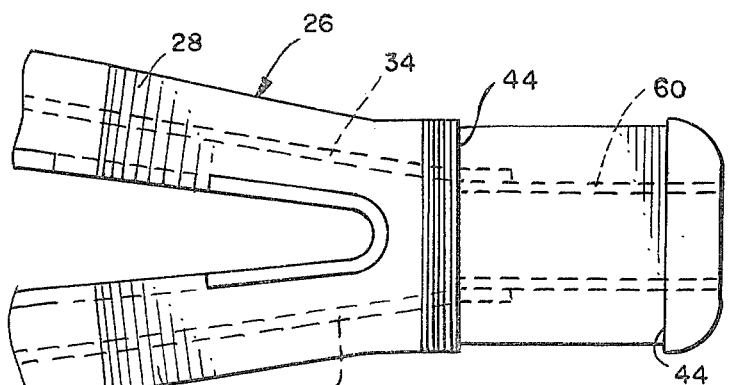
FIG. 7 is a fragmented top plan view of the structure shown in FIG. 6.
Figure 6:
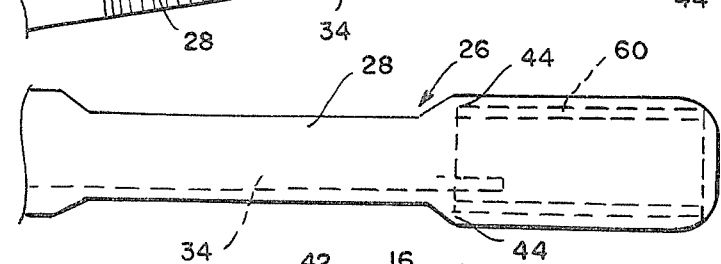
FIG. 6 is a fragmented rear-end elevational view of the terminal clip, including a female connector or socket for a complementary male connector member of a lead wire.

Referring to FIGS. 6 and 7, a modified form of the invention is shown wherein the conductor legs 34 leading from the conductive loops 32 (not shown) terminate abruptly (without the conductor rings 36, FIGS. 4 and 5) and are secured electrically to a female connector or socket 60. The socket is embedded within the dielectric plastic material of the terminal clip body member 26. The female socket 60 is adapted for receiving a complementary male connector plug electrically secured to the terminal end of the lead wire or cable 28 (not shown). The strain relief cover 50, for use with this male-female connector means might include abutment means for holding the male connector or plug within the female socket 60. In either instance, the cover 50 provides a strain relief for the connection between the electrical conductor legs 34 which lead forwardly to the conductive loops 32.

It will be understood that the invention may be embodied in other specific forms without departing from the spirit or central characteristics thereof. The present examples and embodiments, therefore, are to be considered in all respects as illustrative and not restrictive, and the invention is not to be limited to teh details given herein but may be modified within the scope of the appended claims.

We claim:

1. A terminal clip for use with electrodes of the general type having a male projection with an enlarged diameter head portion thereon, said male projection being disposed within a recessed area in the electrode, comprising:
    a pair of support arms integrally formed of resilient dielectric plastic material in an initial unstressed generally V-shape so that the arms are secured together at one end and normally spaced from each other at the other end, said arms having offset depending shoulder portions spaced from said one end and which are positionable within said recessed area of said electrode when the arms are moved toward each other; and
    a conductive loop extending inwardly from the depending shoulder portion of each of said arms toward the other arm and overlappable with each other when the arms are moved toward each other to form an aligned aperture sufficiently large to pass over said head portion when so overlapped, said conductive loops being defined by an offset end of a flat, thin, generally L-shaped integral conductive member embedded within said dielectric plastic arms, with offset ends of the L-shaped conductive members extending into the offset depending shoulder portions of said arms, and with the legs of the L-shaped conductive members extending along and within the support arms to said one ends thereof for connection to a lead wire or the like.

2. The terminal clip of claim 1 including a generally V-shaped spring disposed between said arms generally at the apex of the V-shape thereof, to provide additional resiliency to accomodate for any resilient memory of said dielectric plastic material.

3. The terminal clip of claim 1 wherein said loops are resilient so as to deflect under said head portion to pivotally move about an axis generally parallel to said arms and spaced from the center of said head portion to accomodate movement of the clip away from said electrode without disassembly therefrom.

4. The terminal clip of claim 1 wherein at least one of said arms has a shelf projecting toward the other arm over at least a portion of its respective conductive loop to cover at least a portion of said head portion when the loops are so overlapped.

5. A terminal clip for use with instruments such as medical monitoring instruments, or the like, comprising:
    a terminal body member connected at one end thereof to a lead wire;
    identification means, such as for identifying anatomical positions or the like, on said terminal body member adjacent said one end, said identification means comprising a member removably positionable on said terminal body member for replacing or interchanging the identification means to permit different anatomical positions, or the like, to be identified; and
    a strain relief cover member positionable over said one end of said body member to provide a strain relief over the connection to said lead wire and over said identification means, said cover member at least in part being transparent to provide visual observation of said identification means through the strain relief cover, and said cover member being removably mounted on said one end of said terminal body member by complementary means between the strain relief cover member and the terminal body member to permit ready removal and interchanging of the identification means thereunder.

6. A terminal clip for use with instruments such as medical monitoring instruments, or the like, comprising:
    a terminal body member connected at one end thereof to a lead wire, said body member including a pair of support arms secured together at one end and normally spaced from each other at the other end;
    a conductive loop extending from each of said arms toward the other arm and overlappable with each other when the arms are moved toward each other to form an aligned aperture for engaging an electrode or the like, said loops being electrically connected to said lead wire;
    identification means, such as for identifying anatomical positions or the like, on said terminal body member adjacent said one end; and
    a strain relief cover member positionable over said one end of said body member and over said identification means to provide strain relief for the connection of said lead wire, and said cover member at least in part being transparent to provide visual observation of said identification means through the cover.

7. The terminal clip of claim 6 wherein said terminal clip is adapted for use with a lead wire having a male connector member, or the like, on the end thereof, and including a female connector member within said one end of said terminal body member for connection to the male connector member of said lead wire, said strain relief cover member providing strain relief about said connection.

8. A terminal clip for use with electrodes of the general type having a male projection with an enlarged diameter head portion thereon, comprising:
- a pair of support arms secured together at one end and normally spaced from each other at the other end, said support arms being integrally formed of resilient dielectric plastic material in an initial unstressed generally V-shape, with releasable connector means being embedded in the plastic material at said one end of said arms;
- a conductive loop extending from each of said arms toward the other arm and overlappable with each other when the arms are moved toward each other to form an aligned aperture sufficiently large to pass over said head portion when so overlapped;
- releasable connector means at said one end of said arms for releasably receiving a complementary connector means of a lead wire;
- electrical conductor means connected between said conductive loops and said releasable connector means;
- identification means on said terminal clip at said one end of said integrally formed support arms, such as for identifying anatomical positions or the like; and
- a strain relief cover positionable over said one end of said integrally formed support arms and over said identification means to provide strain relief for the connection of said lead wire, and said cover member at least in part being transparent to provide visual observation of said identification means.

9. The terminal clip of claim 8 wherein said identification means is removably positionable on said one end of said integrally formed support arms for replacing or interchanging the identification means to permit different anatomical positions, or the like, to be identified.

10. The terminal clip of claim 9 wherein said strain relief cover member is removably mounted on said one end of said support arms to facilitate changing of said identification means.

* * * * *